(12) United States Patent
Klee et al.

(10) Patent No.: US 12,097,271 B2
(45) Date of Patent: Sep. 24, 2024

(54) DENTAL COMPOSITION

(71) Applicant: DENTSPLY DETREY GMBH, Constance (DE)

(72) Inventors: Joachim E. Klee, Radolfzell (DE); Matthias Worm, Singen (DE)

(73) Assignee: DENTSPLY SIRONA INC., York, PA (US)

(*) Notice: Subject to any disclaimer, the term of this patent is extended or adjusted under 35 U.S.C. 154(b) by 478 days.

(21) Appl. No.: 17/601,862

(22) PCT Filed: Apr. 9, 2020

(86) PCT No.: PCT/EP2020/060232
§ 371 (c)(1),
(2) Date: Oct. 6, 2021

(87) PCT Pub. No.: WO2020/208175
PCT Pub. Date: Oct. 15, 2020

(65) Prior Publication Data
US 2022/0192931 A1    Jun. 23, 2022

(30) Foreign Application Priority Data
Apr. 11, 2019  (EP) .................................... 19168755

(51) Int. Cl.
*A61K 6/54* (2020.01)
*A61K 6/60* (2020.01)
(Continued)

(52) U.S. Cl.
CPC .................. *A61K 6/54* (2020.01); *A61K 6/60* (2020.01); *A61K 6/891* (2020.01); *C08L 63/00* (2013.01)

(58) Field of Classification Search
CPC ................................. A61K 6/891; A61K 6/54
See application file for complete search history.

(56) References Cited

U.S. PATENT DOCUMENTS 4,243,763 A * 1/1981 Argentar .............. A61L 24/001
525/38
5,624,976 A   4/1997 Klee
(Continued)

FOREIGN PATENT DOCUMENTS

| EP | 0084784 A1 * | 8/1983 |
| JP | 2009215518 A | 9/2009 |
| JP | 2015147941 A * | 8/2015 |

OTHER PUBLICATIONS

English machine translation of Abe et al (JP 2015-147941). (Year: 2015).*

(Continued)

*Primary Examiner* — Michael F Pepitone
(74) *Attorney, Agent, or Firm* — DENTSPLY SIRONA INC.

(57) ABSTRACT

Dental root canal filling composition comprising
(a) one or more diepoxides;
(b) one or more primary monoamines and/or disecondary diamines;
(c) a particulate filler,
wherein the one or more diepoxides are selected from compounds of the following formula (I) or a salt thereof:

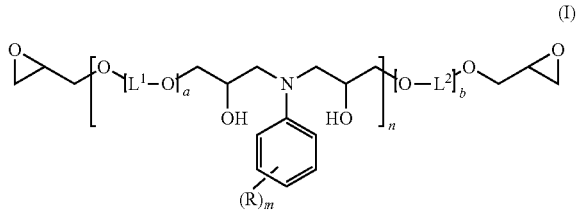

16 Claims, 1 Drawing Sheet

(51) Int. Cl.
    *A61K 6/891*     (2020.01)
    *C08L 63/00*     (2006.01)

(56) References Cited

U.S. PATENT DOCUMENTS

2008/0234404 A1    9/2008    Klee
2017/0156992 A1    6/2017    Klee

OTHER PUBLICATIONS

English machine translation of Eimers et al. (EP 0 084 784) (Year: 1983).*
International Search Report; PCT/EP2020/060232; May 18, 2020 (completed); Jun. 16, 2020 (mailed).
Written Opinion of the International Searching Authority; PCT/EP2020/060232; May 18, 2020 (completed); Jun. 16, 2020 (mailed).
"Investigation of QCM Sensors with Azobenzene Functionalized Coatings for the Detection of Nitroaromatics"; Timothy Ponrathnam et al.; Journal of Macromolecular Science; Part A—Pure and Applied Chemistry; vol. 48, No. 12; Nov. 1, 2011; pp. 1031 to 1037.
European search report; EP 19168755; Oct. 9, 2019 (completed).

\* cited by examiner

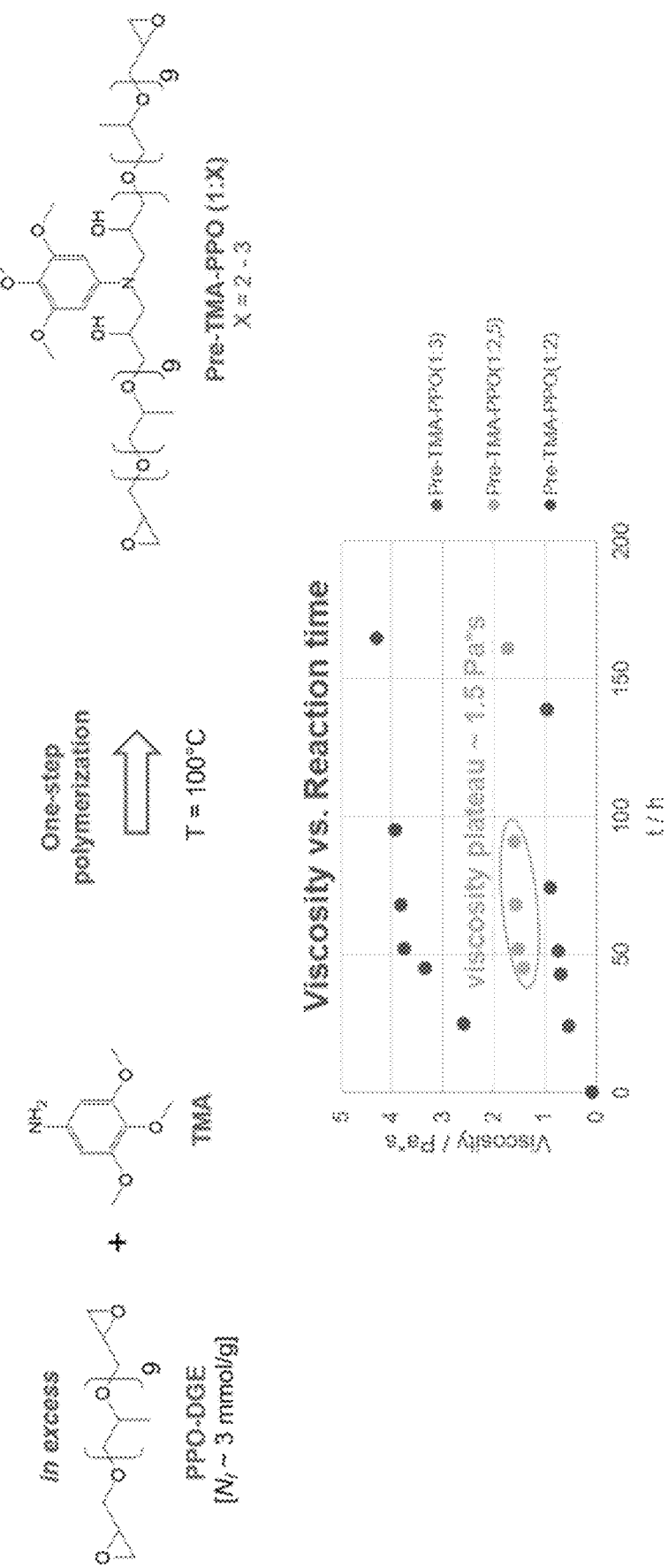

DENTAL COMPOSITION

FIELD OF THE INVENTION

The present invention relates to a dental root canal filling composition comprising a specific diepoxide compound. Furthermore, the present invention relates to a specific diepoxide and to the use of the specific diepoxide compound in the treatment of endodontic disease. Moreover, the present invention relates to a process for preparing a specific diepoxide compound. Finally, the present invention relates to a storage-stable two-pack dental root canal filling composition, wherein the two packs each have a dynamic viscosity at 23° C. which differ by less than 20 Pa·s.

A dental root canal filling in accordance with the invention is adapted to form epoxide-amine addition polymers.

BACKGROUND OF THE INVENTION

Dental compositions in general are desired to approach natural tooth structure with regard to strength and appearance. Accordingly, a great effort is documented by the prior art, which is directed to the development of dental compositions having improved properties with regard to physical and mechanical properties, biocompatibility, aesthetics and handling properties.

Dental compositions which are root canal filling compositions are subject to additional requirements in that the cured product is required to have a high radiopacity and in that the composition may not require external irradiation for curing. Moreover, it is desirable that the composition adheres to the wall of the root canal in order to further improve the tight sealing of the dental root canal. Given that the shape of the root canal may change as a result to mastication and temperature changes, the cured composition must tolerate such changes without compromising a tight seal of the root canal.

Accordingly, in order to provide such additional properties, a root canal filling composition contains radiopaque particulate fillers dispersed in a curable matrix. However, the dispersion of radiopaque particulate fillers gives rise to a stability problem of the dispersions due to the high density of the filler and the low viscosity of the curable matrix.

Moreover, in order to be able to cure a root canal filling composition in the absence of light, the composition is cured by a thermal curing mechanism which may involve step growth polymerizing epoxide precursor compounds.

Prior art dental filling materials for tooth root canals have relatively long setting time, high viscosity, and discolour. Furthermore, epoxide and the amine pastes of prior art two-pack dental root canal filling compositions may have different consistence and give rise to separation problems, which may further result in handling problems during the use of the two-pack dental root canal filling composition.

U.S. Pat. No. 5,624,976 discloses a root canal sealing dental filling composition, wherein specific amines and epoxides are used and amine-epoxide addition polymers are formed during curing.

The gold standard of dental root canal filling material, which presently offers the best overall properties, is AH Plus® (Dentsply DeTrey, Konstanz/Germany). The good overall properties of AH Plus® especially concern physical and mechanical properties, curing properties like gelation time and handling properties like flow- and viscosity properties. The good overall properties highly depend on the filler composition and on the structure of the epoxide-amine addition polymer, which is formed during the curing process of the AH Plus® composition. The AH Plus® dental root canal filling composition consists of an amine paste and an epoxide paste. The AH Plus® epoxide paste comprises Bisphenol A diglycidylether (CAS: 25068-38-6) as a main ingredient. Therefore, large parts of the epoxide-amine addition polymer formed during the curing process of the AH Plus® composition are based on the bisphenol A moiety. Due to this fact, the good overall properties of the AH Plus® composition highly depend on the bisphenol A moiety.

However, bisphenol A is a known endocrine disrupter which can mimic estrogen and may lead to negative health effects. More specifically, bisphenol A mimics the structure and function of the hormone estradiol with the ability to bind to and activate the same estrogen receptor as the natural hormone. Based on the functional relevance of bisphenol-A it is considered that bisphenol-A might contribute to the development of breast cancer. Accordingly, regulatory bodies might determine safety levels of bisphenol-A for humans so that the use of bisphenol A based materials containing bisphenol A in a dental composition cannot be continued in the future.

SUMMARY OF TH INVENTION

It is the problem of the present invention to provide a dental root canal filling composition having excellent properties with regard to physical and mechanical properties, biocompatibility, aesthetics and handling properties.

It is a further problem of the present invention to provide a dental root canal filling composition having a high radiopacity, a high storage stability, a low shrinkage and flexibility, a relatively short setting time, and which may be cured in the absence of light.

Furthermore, it is a problem of the present invention to provide a dental root canal filling composition which has adjustable working and setting times, suitable viscosity, and which shows no coloration problems.

It is a further problem of the present invention to provide a dental root canal filling composition which is cost efficient, simple and available on a scale which is industrially relevant.

Moreover, it is a problem of the present invention to provide a two-pack dental root canal filling composition, wherein the amine and the epoxide paste exhibit sufficient miscibility, and therefore handling problems can be avoided.

It is a further problem of the present invention to provide a dental root canal filling composition which has comparable and/or improved overall properties compared to the AH Plus® composition and which is at the same time bisphenol A free.

It was found that the problems of the present invention can be solved by a dental root canal filling composition comprising (a) one or more diepoxides;

(b) one or more primary monoamines and/or disecondary diamines;

(c) a particulate filler, wherein the one or more diepoxides are selected from compounds of the following formula (I) or a salt thereof:

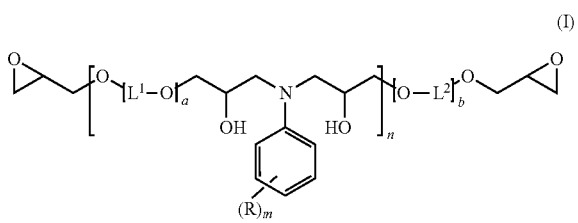

(I)

wherein
R which may be the same or different when more than one R is present, represents a hydroxyl group, a $C_{1-6}$ alkoxy group, a $C_{1-6}$ alkyl group a di-$C_{1-6}$-alkylamino group, or a $C_{6-10}$ aryl group, or two R may be linked together and form with the carbon atoms to which they are bonded a 5- to 7-membered ring which may contain 1 or 2 heteroatoms selected from oxygen atoms and sulfur atoms;

$L^1$ and $L^2$ which may be the same or different when more than one of $L^1$ and $L^2$ is present, independently represent a divalent saturated $C_{2-10}$ hydrocarbyl group or a polysiloxane group;

a is an integer of at least 1:
b is an integer of at least 2;
m is an integer of from 1 to 3; and
n is an integer of from 1 to 1000.

It was found that by using one or more diepoxides according to formula (I), which do not comprise a bisphenol A moiety, a dental root canal filling composition can be provided, which has comparable and/or improved overall properties compared to the AH Plus® composition. Therefore, the dental root canal filling composition has an improved biocompatibility compared to AH Plus® or other bisphenol A containing dental root canal filling compositions.

Furthermore, the present invention provides a dental root canal filling composition wherein the one or more diepoxides of component (a) have a dynamic viscosity at 23° C. of less than 10 Pa·s.

It was found that one or more diepoxides of component (a) which have a dynamic viscosity at 23° C. of less than 10 Pa·s are especially useful in two-pack dental root canal filling compositions. It was found that the use of one or more diepoxides having such a low viscosity leads to a sufficient miscibility of the epoxide paste with commonly used amine pastes, and therefore handling problems during the use of the two-pack dental root canal filling composition can be avoided.

Furthermore, it was found that the use of diepoxides having a dynamic viscosity at 23° C. of less than 10 Pa·s in a dental root canal filling composition leads to an excellent storage stability of the dental root canal filling composition.

Moreover, the present invention provides a diepoxide of the following formula (I) or a salt thereof:

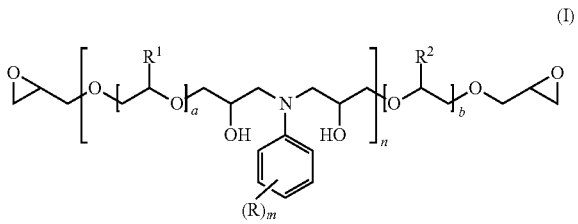

(I)

wherein
R which may be the same or different when more than one R is present, represents a hydroxyl group, a $C_{1-6}$ alkoxy group, a $C_{1-6}$ alkyl group a di-$C_{1-6}$-alkylamino group, or a $C_{6-10}$ aryl group, or two R may be linked together and form with the carbon atoms to which they are bonded a 5- to 7-membered ring which may contain 1 or 2 heteroatoms selected from oxygen atoms and sulfur atoms;

$R^1$ and $R^2$ which may be the same or different when more than one of $R^1$ and $R^2$ is present, represent a hydrogen atom or a $C_{1-6}$ alkyl group;

a is an integer of at least 1;
b is an integer of at least 2;
m is an integer of from 1 to 3; and
n is an integer of from 1 to 1000.

Furthermore, the present invention provides the use of the diepoxide of the present invention for use in the treatment of endodontic disease.

Moreover, the present invention provides a process for preparing a diepoxide of the present invention, which comprises reacting one or more compounds of the following formula (II):

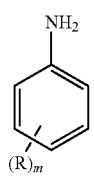

(II)

wherein R and m are as defined above, with an excess of one or more compounds of the following formula (III)

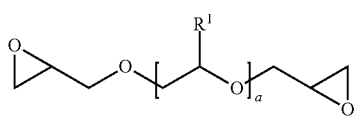

(III)

wherein $R^1$ and a are as defined above.

Finally, the present invention provides a storage-stable two-pack dental root canal filling composition comprising a first paste and a second paste, which pastes each having a dynamic viscosity at 23° C. which differ by less than 20 Pa·s, wherein the dental root canal filling composition is a composition as defined herein.

It was found that a small difference in the viscosities of less than 20 Pa·s between the first and the second paste leads to a sufficient miscibility of the first paste and the second paste, and therefore handling problems during the use of the two-pack dental root canal filling composition can be avoided. Furthermore, it was found that such two-pack dental root canal filling compositions exhibit excellent storage stabilities.

The present invention is based on the recognition that a dental root canal filling composition comprising one or more diepoxides according to formula (I) provides a bisphenol A free dental root canal filling composition which has comparable and/or improved overall properties and an improved biocompatibility compared to the AH Plus® composition. Moreover, the present invention is based on the recognition that a dental root canal filling composition comprising a compound of formula (I) provides a dental root canal filling composition having excellent properties with regard to physical and mechanical properties, biocompatibility, aesthetics, handling properties, having a high radiopacity, a high storage stability, a low shrinkage and flexibility, a relatively short setting time, and may be cured in the absence of light. Furthermore, the dental root canal filling composition according to the present invention provides adjustable working and setting times, suitable viscosity, and shows no coloration problems. Moreover, the present invention provides a curable dental root canal filling composition which is cost efficient, simple and available on a scale which is industrially relevant.

The one or more diepoxides selected from compounds of formula (I), can be used to provide an epoxide paste which has an advantageously low viscosity. The low viscosity of the epoxide paste in general leads to a dental root canal filling composition with a better storage stability. Furthermore, the diepoxides selected from compounds of formula (I), can be used to provide a storage-stable two-pack dental root canal filling composition, wherein the difference of the dynamic viscosities between the epoxide paste and the amine paste can be kept very small, which leads to a better miscibility of the two pastes and therefore to better handling properties of the two-pack composition.

BRIEF DESCRIPTION OF THE FIGURES

FIG. 1 shows the synthesis of epoxide-functional prepolymers (Pre-TMA-PPO) and monitoring of viscosity.

DETAILED DESCRIPTION OF PREFERRED EMBODIMENTS

The present invention relates to a dental root canal filling composition comprising a specific diepoxide compound. A dental root canal filling in accordance with the invention is adapted to form epoxide-amine addition polymers. Furthermore, the present invention relates to a specific diepoxide and to the use of the specific diepoxide compound in the treatment of endodontic disease. Moreover, the present invention relates to a process for preparing a specific diepoxide compound. Finally, the present invention relates to a storage-stable two-pack dental root canal filling composition, wherein the two packs each have a dynamic viscosity at 23° C. which differ by less than 20 Pa·s.

The terms "polymerization" and "polymerizable" relate to the combining by covalent bonding of a large number of smaller molecules, such as monomers, to form larger molecules, that is, macromolecules or polymers. The monomers may be combined to form only linear macromolecules or they may be combined to form three-dimensional macromolecules, commonly referred to as crosslinked polymers. For example, difunctional monomers form linear polymers, whereas monomers having at least three functional groups form crosslinked polymers also known as networks. In case of a higher conversion rate of the polymerizable monomer, the amount of multifunctional monomers may be reduced or the leaching problem may be alleviated.

The term "curing" means the polymerization of functional polymerizable compounds such as monomers, oligomers or even polymers, into a polymer network, preferably a crosslinked polymer network.

The "working time" is the time between the beginning of the setting reaction when the polymer and modified particulate reactive filler are combined in the presence of water, and the time the setting reaction proceeds to the point when it is no longer practical to perform further physical work upon the system, e.g. spatulate it or reshape it, for its intended dental or medical application.

The "setting time" is the time measured from the beginning of the setting reaction in a restoration to the time sufficient hardening has occurred to allow subsequent clinical or surgical procedures to be performed on the surface of the restoration. In a setting reaction, due to the presence of polymerizable groups, a polymerization reaction takes place. In addition to the polymerization reaction, in a glass ionomer cement, the setting reaction additionally involves neutralization of acid groups, for example of polymerizable compounds, by a base in the form of a reactive particulate glass.

The term "storage stability" as used herein means that the dental composition keeps its characteristics, in particular its working time and setting time, even after a long storage time of for example about 2 years.

The One or More Diepoxides

The dental root canal filling composition according to the present invention comprises one or more diepoxides, wherein the one or more diepoxides are selected from compounds of the following formula (I) or a salt thereof:

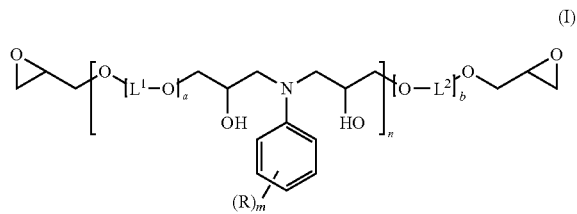

(I)

wherein
R which may be the same or different when more than one R is present, represents a hydroxyl group, a $C_{1-6}$ alkoxy group, a $C_{1-6}$ alkyl group a di-$C_{1-6}$-alkylamino group, or a $C_{6-10}$ aryl group, or two R may be linked together and form with the carbon atoms to which they are bonded a 5- to 7-membered ring which may contain 1 or 2 heteroatoms selected from oxygen atoms and sulfur atoms;
$L^1$ and $L^2$ which may be the same or different when more than one of $L^1$ and $L^2$ is present, independently represent a divalent saturated $C_{2-10}$ hydrocarbyl group or a polysiloxane group;
a is an integer of at least 1;
b is an integer of at least 2;
m is an integer of from 1 to 3; and
n is an integer of from 1 to 1000.

The diepoxide is a compound of formula (I) or a salt thereof, preferably the diepoxide is a compound of formula (I).

In a compound of formula (I), R which may be the same or different when more than one R is present, represents a hydroxyl group, a $C_{1-6}$ alkoxy group, a $C_{1-6}$ alkyl group, a di-$C_{1-6}$-alkylamino group, or a $C_{6-10}$ aryl group, or two R may be linked together and form with the carbon atoms to which they are bonded a 5- to 7-membered ring which may contain 1 or 2 heteroatoms selected from oxygen atoms and sulfur atoms.

Preferably, R is a hydroxyl group, a $C_{1-6}$ alkoxy group, a $C_{1-6}$ alkyl group a di-$C_{1-6}$-alkylamino group, or a $C_{6-10}$ aryl group, more preferably R is a hydroxyl group, a $C_{1-6}$ alkoxy group, a $C_{1-6}$ alkyl group, or a di-$C_{1-6}$-alkylamino group, even more preferable R is a $C_{1-6}$ alkyl group, or a $C_{1-6}$ alkoxy group, in particular R is a $C_{1-6}$ alkoxy group.

In a particularly preferred embodiment, R is a $C_{1-3}$ alkoxy group, and even more preferred R is a methoxy group.

In a compound of formula (I), $L^1$ and $L^2$ which may be the same or different when more than one of $L^1$ and $L^2$ is present, independently represent a divalent saturated $C_{2-10}$ hydrocarbyl group or a polysiloxane group.

Preferably, $L^1$ and $L^2$ independently represent a divalent saturated $C_{2-10}$ hydrocarbyl group.

The divalent saturated $C_{2-10}$ hydrocarbyl group according to $L^1$ and $L^2$ may be an $C_{2-10}$ hydrocarbyl group which contains up to 5 heteroatoms selected from the group of O, S and N. The divalent saturated $C_{2-10}$ hydrocarbyl group according to $L^1$ and $L^2$ may be an $C_{2-10}$ aliphatic group or a $C_{3-10}$ cycloaliphatic group.

In a preferred embodiment, the divalent saturated $C_{2-10}$ hydrocarbyl group according to $L^1$ and $L^2$ is a $C_{2-10}$ aliphatic group, more preferably a $C_{2-6}$ aliphatic group, even more preferably a $C_{2-4}$ aliphatic group, still more preferably a $C_{2-3}$ aliphatic group, and most preferably a $C_3$ aliphatic group.

In a particularly preferred embodiment, the divalent saturated $C_{2-10}$ hydrocarbyl group according to $L^1$ and $L^2$ is the following group:

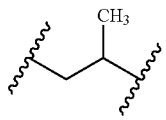 [SMILES: *CC(*)C]

In a preferred embodiment, the divalent saturated $C_{2-10}$ hydrocarbyl group according to $L^1$ and $L^2$ is a $C_{3-10}$ cycloaliphatic group, more preferably a $C_{3-6}$ cycloaliphatic group, even more preferably a $C_{4-6}$ cycloaliphatic group, and in particular a $C_6$ cycloaliphatic group.

In a preferred embodiment, the divalent saturated $C_{2-10}$ hydrocarbyl group according to $L^1$ and $L^2$ is a polysiloxane group. Preferably, the polysiloxane group according to $L^1$ and $L^2$ is a group of the formula $[-OSiR'_2]_z$, wherein R' represents a $C_{1-4}$ alkyl group and z is an integer of from 2 to 20, preferably z is an integer of from 2 to 10, more preferably an integer of from 2 to 6.

In a compound of formula (I), a is an integer of at least 1, preferably a is an integer of from 1 to 20, more preferably a is an integer of from 1 to 10, even more preferably a is an integer of from 5 to 10, in particular a is 9.

In a compound of formula (I), b is an integer of at least 2, preferably b is an integer of from 2 to 20, more preferably b is an integer of from 2 to 10, even more preferably b is an integer of from 5 to 10, in particular b is 9.

In a compound of formula (I), m is an integer of from 1 to 3, preferably m is an integer of from 2 to 3, more preferably m is 3.

In a compound of formula (I), n is an integer of from 1 to 1000, preferably n is an integer of from 1 to 500, more preferably n is an integer of from 1 to 100, even more preferably n is an integer of from 1 to 50, in particular n is an integer of from 1 to 10.

In an embodiment of the present invention, the one or more diepoxides are a salt of the compound of formula (I). The salt of the compound of formula (I) may be any salt, which is suitable for dental applications.

Furthermore, the present invention provides a dental root canal filling composition, wherein the compound of formula (I) or a salt thereof is obtainable by reacting one or more compounds of the following formula (II):

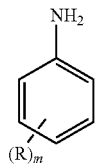

wherein R and m are as defined as in formula (I), with an excess of one or more compounds of the following formula (III)

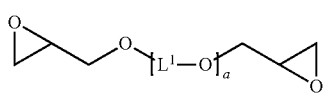

wherein $L^1$ and a are as defined as in formula (I).

If a salt of the compound of formula (I) is synthesized by the process described above, after reacting the compound of formula (II) and the compound of formula (III), subsequently an acid is added to form a salt of the compound of formula (I).

Moreover, the present invention provides a dental root canal filling composition, wherein the diepoxide is a compound of the following formula IA or a salt thereof:

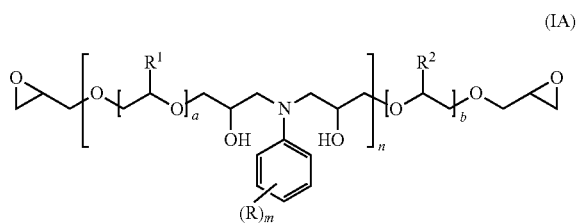

wherein
R which may be the same or different when more than one R is present, represents a hydroxyl group, a $C_{1-6}$ alkoxy group, a $C_{1-6}$ alkyl group a di-$C_{1-6}$-alkylamino group, or a $C_{6-10}$ aryl group, or two R may be linked together and form with the carbon atoms to which they are bonded a 5- to 7-membered ring which may contain 1 or 2 heteroatoms selected from oxygen atoms and sulfur atoms;
$R^1$ and $R^2$ which may be the same or different when more than one of $R^1$ and $R^2$ is present, represent a hydrogen atom or a $C_{1-6}$ alkyl group;
a is an integer of at least 1;
b is an integer of at least 2;
m is an integer of from 1 to 3; and
n is an integer of from 1 to 1000.

In one embodiment of the present invention, the diepoxide is a compound of formula (IA) or a salt thereof, preferably the diepoxide is a compound of formula (IA).

In a compound of formula (IA), R is defined according to the definition of R in formula (I).

In a compound of formula (IA). $R^1$ and $R^2$ which may be the same or different when more than one of $R^1$ and $R^2$ is present, represent a hydrogen atom or a $C_{1-6}$ alkyl group. Preferably, $R^1$ and $R^2$ represent a hydrogen atom or a $C_{1-3}$ alkyl group, more preferably $R^1$ and $R^2$ represent a hydrogen atom or a $C_1$ alkyl group, in particular $R^1$ and $R^2$ represent a methyl group.

In a compound of formula (IA), a is defined according to the definition of a in formula (I).

In a compound of formula (IA), b is defined according to the definition of b in formula (I).

In a compound of formula (IA), m is defined according to the definition of m in formula (I).

In a compound of formula (IA), n is defined according to the definition of n in formula (I).

In an embodiment of the present invention, the one or more diepoxides are a salt of the compound of formula (IA). The salt of the compound of formula (IA) may be any salt, which is suitable for dental applications.

Additionally, the present invention provides a dental root canal filling composition, wherein the one or more diepoxides are selected from compounds of the following formula (IB) or a salt thereof:

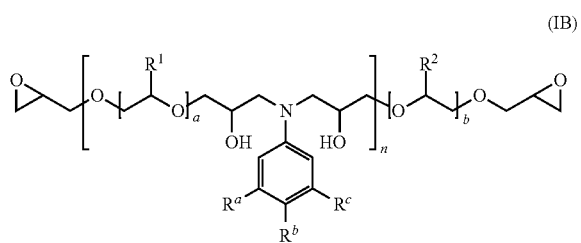

(IB)

wherein $R^a$, $R^b$, and $R^c$ independently have the same meaning as R in formula (I), and $R^1$, $R^2$, a, b, and n are as defined in formula (IA).

In one embodiment of the present invention, the diepoxide is a compound of formula (IB) or a salt thereof, preferably the diepoxide is a compound of formula (IB).

In an embodiment of the present invention, the one or more diepoxides are a salt of the compound of formula (IB). The salt of the compound of formula (IB) may be any salt, which is suitable for dental applications.

In a particularly preferred embodiment, the one or more diepoxides are selected from compounds according to the following formula (IC) or a salt thereof:

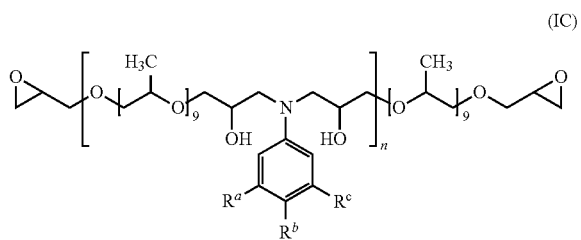

(IC)

wherein $R^a$, $R^b$, and $R^c$ independently have the same meaning as R in formula (I), and n has the same meaning as n in formula (I).

In one embodiment of the present invention, the diepoxide is a compound of formula (IC) or a salt thereof, preferably the diepoxide is a compound of formula (IC).

Preferably, in a compound of formula (IC) $R^a$, $R^b$, and $R^c$ independently represent a hydroxyl group, a $C_{1-6}$ alkoxy group, a $C_{1-6}$ alkyl group a di-$C_{1-6}$-alkylamino group, more preferable $R^a$, $R^b$, and $R^c$ independently represent a $C_{1-6}$ alkyl group, a $C_{1-6}$ alkoxy group, in particular R is a $C_{1-6}$ alkoxy group.

In a particularly preferred embodiment, in a compound according to formula (IC) $R^a$, $R^b$, and $R^c$ independently represent a $C_{1-3}$ alkoxy group, and even more preferred $R^a$, $R^b$, and $R^c$ are methoxy groups.

In an embodiment of the present invention, the one or more diepoxides are a salt of the compound of formula (IC). The salt of the compound of formula (IC) may be any salt, which is suitable for dental applications.

In another particularly preferred embodiment, the one or more diepoxides according to formula (I) is a compound according to the following formula:

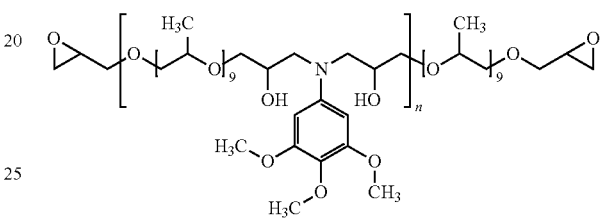

wherein n is defined as in formula (I).

Furthermore, the present invention provides a dental root canal filling composition, wherein the one or more diepoxides of component (a) have a dynamic viscosity at 23° C. of less than 10 Pa·s. Preferably the one or more diepoxides of component (a) have a dynamic viscosity at 23° C. of less than 9 Pa·s, more preferably the one or more diepoxides of component (a) have a dynamic viscosity at 23° C. of less than 8 Pa·s.

Furthermore, the present invention provides a diepoxide according to formula (I) or a salt thereof. Preferably, the present invention provides a diepoxide according to formula (IA) or a salt thereof, more preferably the present invention provides a diepoxide according to formula (IB) or a salt thereof, even more preferably the present invention provides a diepoxide according to formula (IC) or a salt thereof, in particular the present invention provides a diepoxide according to the following formula

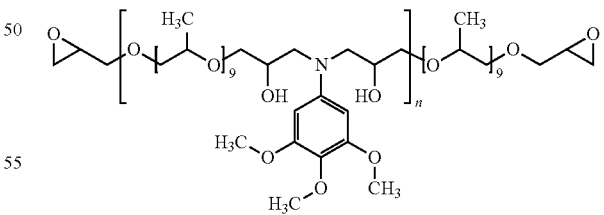

wherein n is defined as in formula (I), or a salt thereof.

In a preferred embodiment, the present invention provides a diepoxide according to formula (I), preferably a diepoxide according to formula (IA), even more preferably a diepoxide according to formula (IB), still more preferably a diepoxide according to formula (IC), in particular the present invention provides a diepoxide according to the following formula

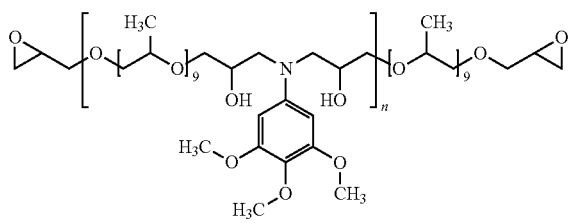

wherein n is defined as in formula (I),

Moreover, the present invention provides a diepoxide of formula (I) or a salt thereof, for use in the treatment of endodontic disease. Preferably, the present invention provides a diepoxide of formula (I), for use in the treatment of endodontic disease.

In a particularly preferred embodiment, the present invention provides a diepoxide compound according to the following formula or a salt thereof

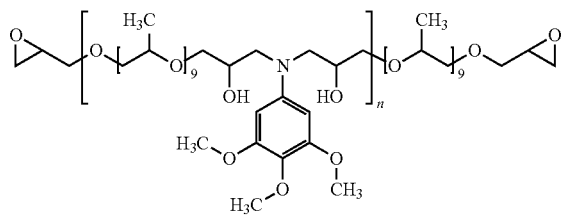

wherein n is defined as in formula (I);
for use in the treatment of endodontic disease.

In a particularly preferred embodiment, the present invention provides a diepoxide compound according to the following formula:

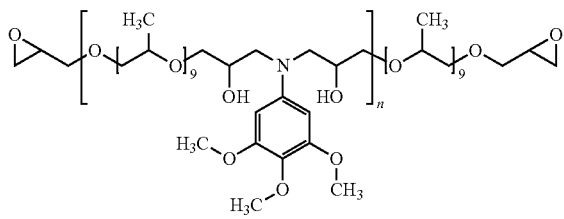

wherein n is defined as in formula (I);
for use in the treatment of endodontic disease.

Additionally, the present invention provides a process for preparing a diepoxide according to formula (I) or a salt thereof, which comprises reacting one or more compounds of the following formula (II):

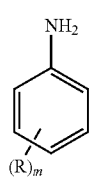

wherein R and m are as defined as in formula (I), with an excess of one or more compounds of the following formula (III)

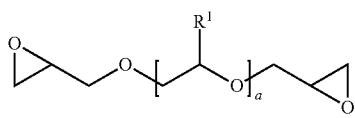

wherein $R^1$ and a are as defined as in formula (I).

If a salt of the compound of formula (I) is synthesized by the process, after reacting the compound of formula (II) and the compound of formula (III), subsequently an acid is added to form a salt of the compound of formula (I).

In a preferred embodiment, according to the present invention in the process for preparing a diepoxide according to formula (I), the compound of formula (II) is 3,4,5-trimethoxy aniline (CAS: 24313-88-0).

The One or More Primary Monoamines and/or Disecondary Diamines

The dental root canal filling composition according to the present invention comprises primary mono- and/or disecondary diamines. The primary mono- and/or disecondary diamines may be any primary mono- and/or disecondary diamines which are suitable in dental applications and/or known in the art.

In a preferred embodiment, the dental root canal filling composition according to the present invention comprises a primary monoamine selected from the group consisting of benzylamine, 1-aminoadamantane, α-phenylethylamine, dimethyl(aminomethyl) phosphine oxide and ethanolamine.

In a preferred embodiment, the dental root canal filling composition according to the present invention comprises a primary monoamine according to the following formula:

Q-NH$_2$ wherein Q is a $C_{2-20}$ hydrocarbyl group which may contain up to 10 heteroatoms selected from the group consisting of O, S, N, and Si. The $C_{2-20}$ hydrocarbyl group may an $C_{2-20}$ alkyl group, a $C_{3-10}$ cycloalkyl group, or a $C_{6-20}$ arylalkyl group. The $C_{2-20}$ hydrocarbyl group may be substituted or unsubstituted. The $C_{2-20}$ hydrocarbyl group may be substituted by hydroxyl groups, tertiary amine groups, halogen atoms, $C_{1-6}$ alkyl groups, $C_{3-10}$ cycloalkyl groups, $C_{5-10}$ aryl groups, $C_{6-11}$ arylalkyl groups, $C_{1-6}$ alkoxy groups.

In a preferred embodiment, the dental root canal filling composition according to the present invention comprises a disecondary diamine selected from the group consisting of N,N'-dibenzylethylenediamine, N,N'-dibenzyl-3,6-dioxaoctandiamine-1,8, N,N'-dibenzyl-5-oxanonandiamine-1,9 (CAS: 113506-22-2), N,N'-dibenzyl-(2,2,4)trimethylhexamethylendiamine, N,N'-dibenzyl-(2,4,4)trimethylhexamethylendiamine.

In a preferred embodiment, the dental root canal filling composition according to the present invention comprises a disecondary diamine according to the following formula (IV):

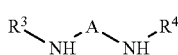

Wherein
A is a divalent substituted or unsubstituted $C_{2-30}$ hydrocarbyl group, and
$R^3$ and $R^4$, which may be the same or different, independently represent a $C_{1-10}$ alkyl group, a $C_{3-10}$ cycloalkyl group, or a $C_{5-11}$ arylalkyl group.

In a compound of formula (IV), A is a divalent substituted or unsubstituted $C_{2-30}$ hydrocarbyl group, which may contain up to 10 heteroatoms selected from the group consisting of N, O, S, Si. Preferably, A is a divalent unsubstituted $C_{2-30}$ hydrocarbyl group.

In one embodiment of the present invention in a compound of formula (IV), A is a divalent substituted $C_{2-30}$ hydrocarbyl group, wherein the substituents are selected from the group consisting of a hydroxyl group, a tertiary amine group, a halogen atom, a $C_{1-6}$ alkyl group, a $C_{3-10}$ cycloalkyl group, a $C_{1-6}$ alkoxy group, a $C_{5-10}$ aryl group, a $C_{5-11}$ arylalkyl group.

In a compound of formula (IV), A represent a divalent substituted or unsubstituted $C_{2-30}$ hydrocarbyl group, wherein the $C_{2-30}$ hydrocarbyl group is a $C_{2-30}$ alkylidene group, a $C_{3-10}$ cycloalkylidene group, a $C_{7-30}$ arylalkylidene group.

In a compound of formula (IV), $R^3$ and $R^4$, which may be the same or different, independently represent $C_{1-10}$ alkyl group, a $C_{3-10}$ cycloalkyl group, or a $C_{6-11}$ arylalkyl group. The $C_{1-10}$ alkyl group, the $C_{3-10}$ cycloalkyl group, or the $C_{6-11}$ arylalkyl group may be substituted or unsubstituted. Preferably, the $C_{1-10}$ alkyl group, the $C_{3-10}$ cycloalkyl group, or the $C_{6-11}$ arylalkyl group is unsubstituted. If the $C_{1-10}$ alkyl group, the $C_{3-10}$ cycloalkyl group, or the $C_{6-11}$ arylalkyl group is substituted, the substituents are selected from the group consisting of a hydroxyl group, a tertiary amine group, a halogen atom, a $C_{1-6}$ alkyl group, a $C_{3-10}$ cycloalkyl group, a $C_{1-6}$ alkoxy group, a $C_{5-10}$ aryl group, or a $C_{6-11}$ arylalkyl group.

The Particulate Filler

The dental root canal filling composition according to the present invention, further comprises a particulate filler. The filler in the dental root canal filling composition according to the present invention may be any filler which is suitable for dental applications and/or known in the art.

In a specific embodiment, the filler according to the present invention is a radiopaque particulate filler. The radiopaque filler according to the present invention may be any radiopaque filler suitable for dental applications and/or known in the art.

The radiopaque particulate filler usually has an average particle size of from 0.005 to 100 µm, preferably of from 0.01 to 40 µm as measured using, for example, by electron microscopy or by using a conventional laser diffraction particle sizing method as embodied by a MALVERN Mastersizer S or MALVERN Mastersizer 2000 apparatus. The radiopaque particulate filler may be a multimodal radiopaque particulate filler representing a mixture of two or more radiopaque particulate fractions having different average particle sizes. The radiopaque particulate filler may also be a mixture of particles of different chemical composition.

The radiopaque filler may be selected from any of the zinc, ytterbium, yttrium, gadolinium, zirconium, strontium, tungsten, tantalum, thorium, niobium, barium, bismuth, molybdenum and lanthanum metals, alloys thereof, organometallic complexes thereof, oxides, sulfates, carbonates, halides, oxy-halides, subnitrates, tungstates and carbides thereof, iodine and inorganic iodides, either singly or in combination. In a preferred embodiment, the radiopaque filler is selected from any of bismuth trioxide, bismuth carbonate, bismuth oxy-chloride, bismuth subnitrate, zirconium oxide, barium sulfate, barium tungstate and calcium tungstate, either singly or in combination. In an even more preferred embodiment, the radiopaque filler is selected from barium tungstate and calcium tungstate, either singly or in combination. Preferably the radiopaque filler is $CaWO_4$.

The dental root canal filling composition according to the present invention preferably comprises 1 to 85 percent by weight, more preferably 40 to 85 percent by weight, even more preferably 40 to 70 percent by weight, of the radiopaque particulate filler, based on the weight of the entire composition.

Further Components

Aliphatic Polyamines

The dental root canal filling composition according to the present invention, may further comprise an aliphatic polyamine. The aliphatic polyamine may be any aliphatic polyamine which is suitable in dental applications and/or known in the art.

In a specific embodiment, the aliphatic polyamine is selected among compounds of the following structures:

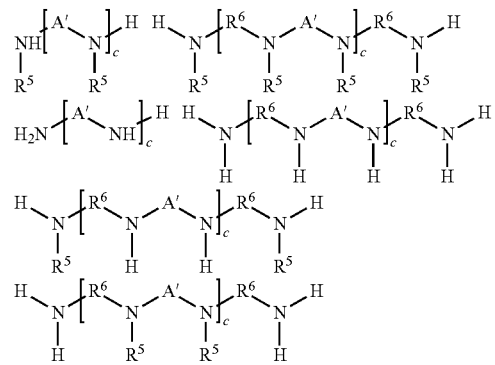

wherein
$R^5$ is hydrogen or a substituted or unsubstituted $C_{1-18}$ alkyl group, a substituted or unsubstituted $C_{3-18}$ cycloalkyl group, or a substituted or unsubstituted $C_{7-18}$ arylalkyl group,
$R^6$ is a difunctional substituted or unsubstituted $C_1$ to $C_{18}$ alkylene group, or a substituted or unsubstituted cycloalkylene group,
A' is a moiety derived from a compound that is capable of an addition reaction with amines such as di- or poly-epoxides, and
c is an integer.

In an aliphatic polyamine according to the structures above, preferably $R^5$ is hydrogen, a substituted or unsubstituted $C_{3-18}$ cycloalkyl group, or a $C_{7-18}$ arylalkyl group. More preferably, $R^5$ is a substituted or unsubstituted $C_{3-18}$ cycloalkyl group, or a substituted or unsubstituted $C_{7-18}$ arylalkyl group. Even more preferably, $R^5$ is a substituted or unsubstituted $C_{7-18}$ arylalkyl group. In a particularly preferred embodiment, $R^5$ is an unsubstituted $C_{7-18}$ arylalkyl group.

In an aliphatic polyamine according to the structures above, preferably $R^6$ is difunctional substituted or unsubstituted $C_1$ to $C_{18}$ alkylene group, more preferably $R^6$ is a difunctional unsubstituted $C_1$ to $C_{18}$ alkylene group.

In an aliphatic polyamine according to the structure above, A' is a moiety derived from a compound that is capable of an addition reaction with amines such as di- or polyepoxides. The di- or polyepoxides may be any di- or polyepoxides suitable for dental applications and/or known in the art. Preferably, A' is a moiety derived from an addition reaction of a diepoxide and amines.

In a preferred embodiment, A' is a moiety derived from an addition reaction of a diepoxide and amines, wherein A' is a moiety which contains one of the following moieties:

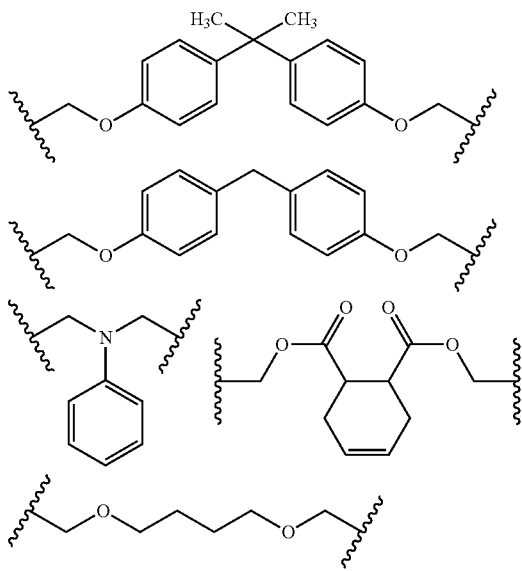

In an aliphatic polyamine according to the structure above, c is an integer. Preferably, c is an integer of from 1 to 10, more preferably c is an integer of from 2 to 8, even more preferably c is an integer of from 4 to 6.

Aliphatic Diamines

In a particularly preferred embodiment, the dental root canal filling composition according to the present invention comprises one or more primary aliphatic diamines. Preferably, the dental root canal composition comprises one primary aliphatic diamine.

Preferably, the primary aliphatic diamines are compounds according to the following formula (V):

(V)

wherein

Q' represents a substituted or unsubstituted $C_{3-20}$ alkylene group or a substituted or unsubstituted $C_{3-20}$ cycloalkylene group, wherein the substituted $C_{3-20}$ alkylene group and the substituted $C_{3-20}$ cycloalkylene group may be substituted by one or more fluorine atoms, hydroxy groups, $C_{1-6}$ alkyl groups, $C_{3-12}$ cycloalkyl groups, a $C_{1-6}$ alkoxy groups, a $C_{1-6}$ alkylthio groups, a $C_{6-10}$ aryl groups, a $C_{6-10}$ aryloxy groups, a $C_{7-14}$ arylalkyl groups, or a $C_{7-14}$ arylalkoxy groups.

In a compound of formula (V), preferably Q' represents a substituted or unsubstituted $C_{3-20}$ cycloalkylene group, more preferably Q' represents a substituted cycloalkylene group, and even more preferably Q' represents a substituted cycloalkylene group, wherein the substituents may be one or more $C_{1-6}$ alkyl groups, $C_{3-12}$ cycloalkyl groups.

In a particularly preferred embodiment, the dental composition according to the present invention comprises a primary aliphatic diamine, which is selected from the group consisting of octahydro-4,7-methano-1H-indenedimethylamine (CAS: 68889-71-4) and isophorone diamine (CAS: 2855-13-2).

One or More Di- or Polyepoxides

The dental root canal filling composition according to the present invention may comprise one or more di- or polyepoxides. The one or more di- or polyepoxides may be any di- or polyepoxides suitable in dental applications and/or known in the art.

In a specific embodiment, the one or more di- or polyepoxides are compound of the following formula (VI):

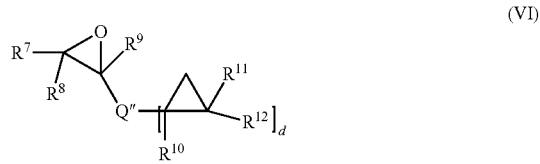

(VI)

wherein

Q" is an (m+1)-valent organic group, $R^7$, $R^8$ and $R^9$ which may be the same or different and which are independent from each other, represent a hydrogen atom, or a $C_{1-6}$ alkyl group, the $R^{10}$, $R^{11}$ and $R^{12}$ which may be the same or different and which are independent from each other, represent a hydrogen atom, or a $C_{1-6}$ alkyl group.

d is an integer of from 1 to 3.

In a compound of formula (VI), Q" represents an (m+1)-valent organic group. Preferably, Q" represents a 2-valent organic group, or a 3-valent organic group, and more preferably, Q" represents a 2-valent organic group.

The (m+1)-valent organic group, may be a group having a total of 1 to 40 carbon atoms, preferably 2 to 20 carbon atoms. The organic group may include an aliphatic, alicyclic, or aromatic moiety or a combination of two or more of such moieties. The organic group may further include one or more functional groups such as amide groups, ester groups, urethane groups, urea groups, keto groups, ether groups, thioether groups, carbonate groups, or tertiary amino groups, which link two or more aliphatic, alicyclic, or aromatic moieties. Furthermore, the organic group may be substituted by one or more substituents selected from hydroxyl groups, halogen atoms, a $C_{1-6}$ alkyl group, a $C_{1-6}$ alkoxy group, a $C_{1-6}$ alkylthio group, a $C_{6-10}$ aryl group, a $C_{6-10}$ aryloxy group, a $C_{7-14}$ arylalkyl group, or a $C_{7-14}$ arylalkoxy group.

Preferably, the (m+1)-valent organic group may include alicyclic or aromatic moiety, and more preferably the (m+1)-valent organic group includes an aromatic moiety.

In one embodiment, Q" represents the following group:

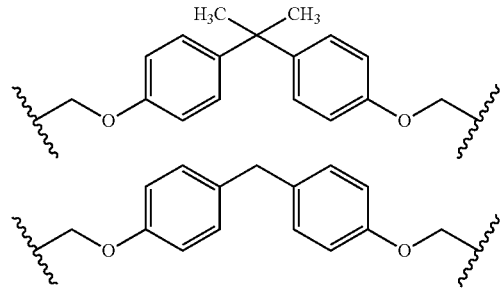

-continued

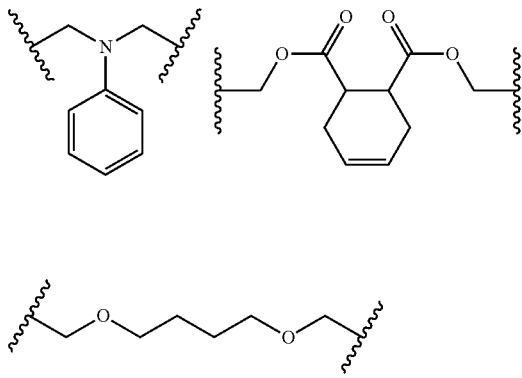

In a compound of formula (VI), m is an integer of from 1 to 3. Preferably, m is an integer of from 1 to 2, and more preferably m is 1.

In a compound of formula (VI), $R^7$, $R^8$ and $R^9$ which may be the same or different and which are independent from each other, represent a hydrogen atom, or a $C_{1-6}$ alkyl group. Preferably, $R^7$, $R^8$ and $R^9$ represent a hydrogen atom. In a particularly preferred embodiment, all three of $R^7$, $R^8$ and $R^9$ represent a hydrogen atom.

In a compound of formula (VI), the $R^{10}$, $R^{11}$ and $R^{12}$ which may be the same or different and which are independent from each other, represent a hydrogen atom, or a $C_{1-6}$ alkyl group. Furthermore, in a compound of formula (VI), if more than one $R^{10}$ is present, the more than one $R^{10}$ may be different. In a compound of formula (VI), if more than one $R^{11}$ is present, the more than one $R^{11}$ may be different. In a compound of formula (VI), if more than one $R^{12}$ is present, the more than one $R^{12}$ may be different. Preferably, $R^{10}$, $R^{11}$ and $R^{12}$ represent a hydrogen atom. In a particularly preferred embodiment, all of the $R^{10}$, $R^{11}$ and $R^{12}$ moieties which are present are hydrogen atoms.

In particularly preferred embodiment, the compound according to formula (VI) is Bis-[4-(-2,3-epoxypropoxy)phenyl]-methane (CAS: 9003-36-5).

Further Optional Components

The dental root canal filling composition according to the present invention may, besides of the above described components, comprise additional optional components. The dental root canal filling composition according to the present invention may optionally contain any additive suitable for dental applications and/or known in the art.

For example, the dental root canal filling composition according to the present invention may comprise water, or any solvent known in the art. The dental root canal filling composition of the present invention may preferably comprise 5 to 20 percent by weight based on the total weight of the composition of water or any solvent known in the art.

Optionally, the dental root canal filling composition may further comprise stabilizer(s), and/or pigments.

The dental root canal filling composition according to the present invention has a gel time of at most 20 hours. Preferably, the dental root canal filling composition according to the present invention has a gel time of at most 18 hours, more preferably the dental root canal filling composition according to the present invention has a gel time of at most 15 hours.

Finally, the present invention provides storage-stable two-pack dental root canal filling composition comprising a first past and a second paste, which pastes each having a dynamic viscosity at 23° C. which differ by less than 20 Pa·s, wherein the dental root canal filling composition is a composition as defined according to the present invention.

The invention will now be further illustrated by the following Examples.

EXAMPLES

In the following section, the preparation of epoxide prepolymers with aromatic amines and characterization of respective paste formulations are presented fulfilling the claimed properties with setting times at body temperature below 16 h, flow behavior comparable to AH Plus® (19-25 mm), elevated resin viscosities of the amine resin and slightly reduced resin of epoxide resin.

Dynamic viscosities may be measured at 23° C. by using a Bohlin CS50 rheometer.

Materials

Polypropylene glycol diglycidyl ether (PPO-DGE, Mn~640 g/mol) and 3,4,5-trimethoxy anillin (TMA) was purchased from Sigma Aldrich. 4,4'-Isopropylidendicyclohexanol diglycidyl ether (DENACOL EX-252, CAS 30583-72-3, η=2.2 Pa*s) was provided by *Nagase Chemistry*. Priamine 1071 and Priamine 1075 (η=0.2 Pa*s) were provided from Crode and used as received. Bisphenol A diglycidyl ether (Araldite GY 250, CAS 25068-38-6) and bisphenol F diglycidyl ether (Araldite GY 285, CAS 9003-36-5). N,N'-Dibenzyl-5-oxanonandi-amin-1,9 (OPC-91) was obtained from *A.M.B. LIFE & SCIENCE ApS*. CaWO$_4$ (1 □m and 6 □m Grade B) particles were purchased from Starck H. C. GmbH and ZrO$_2$ particles (CAS 1314-23-4) were purchased from S. Goldmann GmbH & Co. KG. Aerosil$_{200}$ was provided by CSC Jäkle Chemie. SICOVIT® (Yellow 10 E 172) was purchased from Simon und Werner GmbH. All other chemicals were purchased from common chemical suppliers.

Prepolymer Synthesis

Synthesis of Pre-TMA-PPO(1:2,5) (ASO4-50-02)

3,4,5-trimethoxy anillin (TMA) (2,634 g, 14.375 mmol) and polypropylene glycol diglycidyl ether (PPO-DGE. M$_n$=640 g/mol) (23.013 g, 35.938 mmol) were stirred in a round-bottom flask (100 mL) at 100° C. The final product was obtained in quantitative yield after 187 h exhibiting a viscosity of η=1.47 Pa*s.

TABLE 1

Results of four different epoxide-prepolymer batches Pre-TMA-PPO (1:2.5) showing values of viscosity η and epoxide content $n_f$ of the recovered prepolymers.

| Polymer Composition | Batch Number | Final viscosity η [Pa * s] | Epoxide content $n_f$ qNMR [mmol/g] | Reaction time t [h] |
|---|---|---|---|---|
| Pre-TMA-PPO(1:2.5) | ASO4-49-01 | 1.41 | 1.647 | 187 |
| Pre-TMA-PPO(1:2.5) | ASO4-50-02 | 1.47 | 1.670 | 187 |
| Pre-TMA-PPO(1:2.5) | ASO4-58-01 | 1.54 | 1.600 | 161 |
| Pre-TMA-PPO(1:2.5) | ASO4-105-01 | 1.45 | 1.721 | 161 |

Synthesis of Pre-PPO-OPC91 (ASO449-02)

N,N'-Dibenzyl-5-oxanonandiamin-1,9 (OPC-91) (10.642 g, 31.250 mmol) and polypropylene glycol diglycidyl ether (PPO-DGE, Mn=640 g/mol) (9.993 g, 15.625 mmol) were stirred in a round-bottom flask (100 mL) at 40° C. The final product was obtained in quantitative yield after 71 h exhibiting a viscosity of η=3.8 Pa*s.

Paste Formulations

Paste A.1.
Preparation of Epoxide Paste A1 (ASO4-92-01)

Pre-TMA-PPO(1:2,5) (1.6016 g) and 4,4'-Isopropylidendicyclohexanol diglycidyl ether (1.6031 g) were transferred into a speed mixer container and mixed for 1 min with 2150 rpm under reduced pressure (p=1000 mbar). $CaWO_4$ 1 μm (8.1395 g), Aerosil®$_{200}$ (0.1156 g) and SICOVIT® (Yellow 10 E172) (0.0120 g) were added and speed mixing was applied (1 min, 2150 rpm, 100 mbar). The paste was manually mixed with a spatula followed by another speed mixer run (1 min, 2150 rpm, 100 mbar) to afford a homogenous, light yellow paste. Flow (ISO6876): 20.83 mm.

Preparation of Amine Paste A1 (ASO3-90-02)

Pre-PPO-OPC91(1:2) (2.151 g), Priamine1075 (0.922 g), $CaWO_4$ 1 μm (7.340 g) and Aerosil®200 (0.114 g) were transferred into a speed mixer container and mixed for 1 min with 2150 rpm under reduced pressure (p=1000 mbar). The pastes were manually mixed with a spatula followed by another speed mixer run (1 min, 2150 rpm, 1000 mbar) to afford a homogenous, white paste. Flow (ISO6876): 26.8 mm.

Mixtures of Paste A1 (SAR2-147-01+SAR2-155-01)

Amine Paste A1 and epoxide Paste A1 were mixed in a ratio $m_{Epoxide}/m_{Amine}=1.09795$. The mixed pastes exhibit a setting time of <16 h, flow of 19.8 mm, film thickness of 9 μm (all according to ISO 6876).

The invention claimed is:

1. Dental root canal filling composition comprising
   (a) one or more diepoxides;
   (b) one or more primary monoamines and/or disecondary diamines;
   (c) a particulate filler,
wherein the one or more diepoxides are selected from compounds of the following formula (I) or a salt thereof:

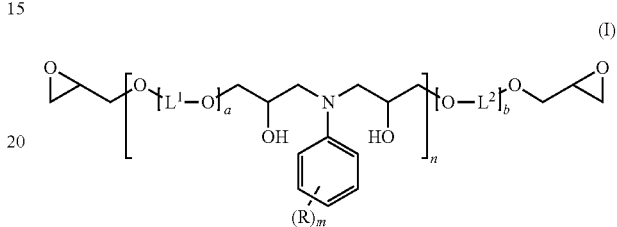

wherein
R which may be the same or different when more than one R is present, represents a hydroxyl group, a $C_{1-6}$ alkoxy group, a $C_{1-6}$ alkyl group, a di-$C_{1-6}$-alkylamino group, or a $C_{6-10}$ aryl group, or two R may be linked together and form with the carbon atoms to which they are bonded a 5- to 7-membered ring which may contain 1 or 2 heteroatoms selected from oxygen atoms and sulfur atoms;
$L^1$ and $L^2$ which may be the same or different when more than one of $L^1$ and $L^2$ is present, independently represent a divalent saturated $C_{2-10}$ hydrocarbyl group or a polysiloxane group;
a is an integer of at least 1;
b is an integer of at least 2;
m is an integer of from 1 to 3; and
n is an integer of from 1 to 1000.

2. The dental root canal filling composition according to claim 1, wherein the compound of formula (I) or a salt thereof is obtained by reacting one or more compounds of the following formula (II):

wherein R which may be the same or different when more than one R is present, represents a hydroxyl group, a $C_{1-6}$ alkoxy group, a $C_{1-6}$ alkyl group, a di-$C_{1-6}$-alkylamino group, or a $C_{6-10}$ aryl group, or two R may be linked together and form with the carbon atoms to which they are bonded a 5- to 7-membered ring which may contain 1 or 2 heteroatoms selected from oxygen atoms and sulfur atoms, and m is an integer of from 1 to 3, with an excess of one or more compounds of the following formula (III)

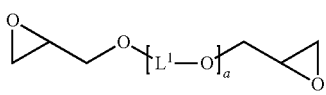

(III)

wherein each $L^1$ independently represents a divalent saturated $C_{2-10}$ hydrocarbyl group or a polysiloxane group and a is an integer of at least 1.

3. The dental root canal filling composition according to claim 1, wherein the diepoxide is a compound of the following formula (IA) or a salt thereof:

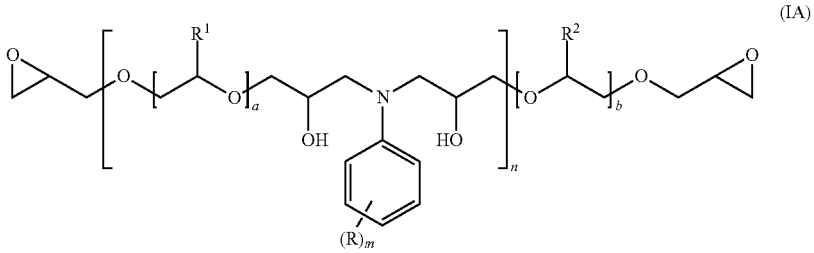

(IA)

wherein
R which may be the same or different when more than one R is present, represents a hydroxyl group, a $C_{1-6}$ alkoxy group, a $C_{1-6}$ alkyl group a di-$C_{1-6}$-alkylamino group, or a $C_{6-10}$ aryl group, or two R may be linked together and form with the carbon atoms to which they are bonded a 5- to 7-membered ring which may contain 1 or 2 heteroatoms selected from oxygen atoms and sulfur atoms;
$R^1$ and $R^2$
which may be the same or different when more than one of $R^1$ and $R^2$ is present, represent a hydrogen atom or a $C_{1-6}$ alkyl group;
a is an integer of at least 1;
b is an integer of at least 2;
m is an integer of from 1 to 3; and
n is an integer of from 1 to 1000.

4. The dental root canal filling composition according to claim 1, wherein m is 3.

5. The dental root canal filling composition according to claim 1, wherein R is a $C_{1-6}$ alkoxy group or a $C_{1-6}$ alkyl group.

6. The dental root canal filling composition according to claim 1, wherein the one or more diepoxides are selected from compounds of the following formula (IB) or a salt thereof:

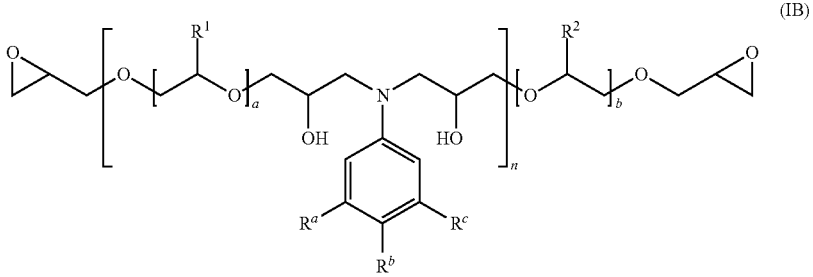

(IB)

wherein $R^a$, $R^b$, and $R^c$ independently represents a hydroxyl group, a $C_{1-6}$ alkoxy group, a $C_{1-6}$ alkyl group a di-$C_{1-6}$-alkylamino group, or a $C_{6-10}$ aryl group, or two of $R^a$, $R^b$, and $R^c$ may be linked together and form with the carbon atoms to which they are bonded a 5- to 7-membered ring which may contain 1 or 2 heteroatoms selected from oxygen atoms and sulfur atoms;
$R^1$ and $R^2$ which may be the same or different when more than one of $R^1$ and $R^2$ is present, represent a hydrogen atom or a $C_{1-6}$ alkyl group;
a is an integer of at least 1;
b is an integer of at least 2;
and n is an integer of from 1 to 1000.

7. The dental root canal filling composition according to claim 1, wherein the one or more diepoxides of component (a) have a dynamic viscosity at 23° C. of less than 10 Pa·s.

8. The dental root canal filling composition according to claim 1, which has a gelation time of less than 20 hours.

9. The dental root canal filling composition according to claim 1, which further comprises an aliphatic polyamine selected among compounds of the following structures:

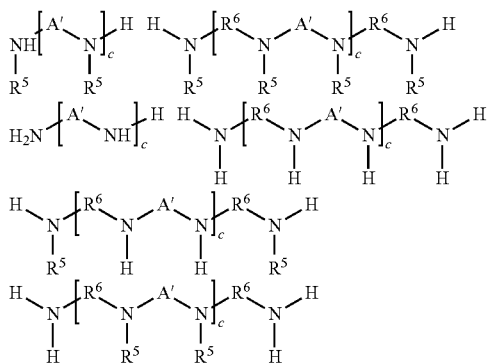

wherein
R⁵ represents hydrogen or a substituted or unsubstituted $C_1$ to $C_{18}$ alkyl group, a substituted or unsubstituted $C_3$ to $C_{18}$ cycloalkyl group, or a substituted or unsubstituted $C_7$ to $C_{18}$ aralkyl group,
R⁶ represents a difunctional substituted or unsubstituted $C_1$ to $C_{18}$ alkylene group, or a substituted or unsubstituted cycloalkylene group,
A' represents a moiety derived from a compound that is capable of an addition reaction with an amine, and
c is an integer.

10. The dental root canal filling composition according to claim 1, wherein the particulate filler (c) comprises $CaWO_4$.

11. A diepoxide of the following formula (I) or a salt thereof:

$$\text{(I)}$$

wherein
R which may be the same or different when more than one R is present, represents a hydroxyl group, a $C_{1-6}$ alkoxy group, a $C_{1-6}$ alkyl group a di-$C_{1-6}$-alkylamino group, or a $C_{6-10}$ aryl group, or two R may be linked together and form with the carbon atoms to which they are bonded a 5- to 7-membered ring which may contain 1 or 2 heteroatoms selected from oxygen atoms and sulfur atoms;
R¹ and R²
which may be the same or different when more than one of R¹ and R² is present, represent a hydrogen atom or a $C_{1-6}$ alkyl group;
a is an integer of at least 1;
b is an integer of at least 2;
m is an integer of from 1 to 3; and
n is an integer of from 1 to 1000.

12. The diepoxide according to claim 11, for use in the treatment of endodontic disease.

13. A process for preparing a diepoxide of the following formula (I) or a salt thereof:

$$\text{(I)}$$

wherein
R which may be the same or different when more than one R is present, represents a hydroxyl group, a $C_{1-6}$ alkoxy group, a $C_{1-6}$ alkyl group a di-$C_{1-6}$-alkylamino group, or a $C_{6-10}$ aryl group, or two R may be linked together and form with the carbon atoms to which they are bonded a 5- to 7-membered ring which may contain 1 or 2 heteroatoms selected from oxygen atoms and sulfur atoms;
R¹ and R²
which may be the same or different when more than one of R¹ and R² is present, represent a hydrogen atom or a $C_{1-6}$ alkyl group;
a is an integer of at least 1;
b is an integer of at least 2;
m is an integer of from 1 to 3; and
n is an integer of from 1 to 1000, which comprises reacting one or more compounds of the following formula (II):

$$\text{(II)}$$

wherein R which may be the same or different when more than one R is present, represents a hydroxyl group, a $C_{1-6}$ alkoxy group, a $C_{1-6}$ alkyl group, a di-$C_{1-6}$-alkylamino group, or a $C_{6-10}$ aryl group, or two R may be linked together and form with the carbon atoms to which they are bonded a 5- to 7-membered ring which may contain 1 or 2 heteroatoms selected from oxygen atoms and sulfur atoms and
m is an integer of from 1 to 3 with an excess of one or more compounds of the following formula (III)

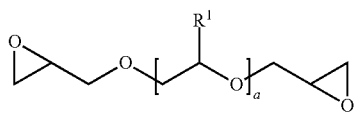

wherein R¹ which may be the same or different when more than one R¹ is present represent a hydrogen atom or a $C_{1-6}$ alkyl group and a is an integer of at least 1.

14. The process according to claim 13, wherein the compound of formula (II) is 3,4,5-trimethoxy aniline.

15. Storage-stable two-pack dental root canal filling composition comprising a first paste and a second paste, wherein each paste has a dynamic viscosity at 23° C. that differs by less than 20 Pa·s from the other paste, wherein the first paste comprises one or more diepoxides selected from compounds of the following formula (I) or a salt thereof:

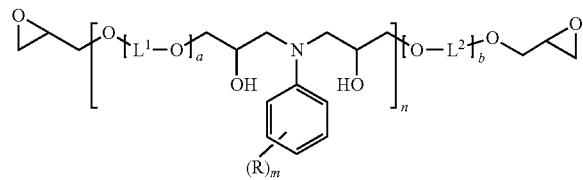

wherein

R which may be the same or different when more than one R is present, represents a hydroxyl group, a $C_{1-6}$ alkoxy group, a $C_{1-6}$ alkyl group, a di-$C_{1-6}$-alkylamino group, or a $C_{6-10}$ aryl group, or two R may be linked together and form with the carbon atoms to which they are bonded a 5- to 7-membered ring which may contain 1 or 2 heteroatoms selected from oxygen atoms and sulfur atoms;

$L^1$ and $L^2$ which may be the same or different when more than one of $L^1$ and $L^2$ is present, independently represent a divalent saturated $C_{2-10}$ hydrocarbyl group or a polysiloxane group;

a is an integer of at least 1;

b is an integer of at least 2;

m is an integer of from 1 to 3; and n is an integer of from 1 to 1000, n and the second paste comprises one or more primary monoamines and/or disecondary amines.

16. The dental root canal filling composition according to claim 9, wherein A' represents a di- or polyepoxide.

\* \* \* \* \*

UNITED STATES PATENT AND TRADEMARK OFFICE
CERTIFICATE OF CORRECTION

PATENT NO. : 12,097,271 B2
APPLICATION NO. : 17/601862
DATED : September 24, 2024
INVENTOR(S) : Klee et al.

Page 1 of 1

It is certified that error appears in the above-identified patent and that said Letters Patent is hereby corrected as shown below:

On the Title Page

In item (71), in "Applicant", in Column 1, Lines 1-2, delete "DENTSPLY DETREY GMBH, Constance (DE)" and insert --DENTSPLY SIRONA INC., York, PA (US)-- therefor In the Claims In Column 26, Line 23, in Claim 15, after "1000,", delete "n"

Signed and Sealed this
Seventeenth Day of December, 2024

Derrick Brent
*Acting Director of the United States Patent and Trademark Office*